US008655034B2

(12) United States Patent
Noda

(10) Patent No.: US 8,655,034 B2
(45) Date of Patent: Feb. 18, 2014

(54) INFORMATION PROCESSING APPARATUS, PROCESSING METHOD, AND COMPUTER-READABLE STORAGE MEDIUM

(75) Inventor: Takeshi Noda, Ebina (JP)

(73) Assignee: Canon Kabushiki Kaisha, Tokyo (JP)

( * ) Notice: Subject to any disclaimer, the term of this patent is extended or adjusted under 35 U.S.C. 154(b) by 80 days.

(21) Appl. No.: 12/971,563

(22) Filed: Dec. 17, 2010

(65) Prior Publication Data

US 2011/0158550 A1    Jun. 30, 2011

(30) Foreign Application Priority Data

Dec. 24, 2009  (JP) ................................. 2009-293208

(51) Int. Cl.
*G06K 9/00* (2006.01)
*G06K 9/40* (2006.01)
(52) U.S. Cl.
USPC ............................ 382/128; 382/265; 382/275
(58) Field of Classification Search
USPC ........................................................ 382/265
See application file for complete search history.

(56) References Cited

U.S. PATENT DOCUMENTS

| 4,847,909 | A | | 7/1989 | Shibata ............................. 382/6 |
| 5,296,937 | A | * | 3/1994 | Nakatani et al. ............... 358/448 |
| 5,799,111 | A | * | 8/1998 | Guissin ........................... 382/254 |
| 5,903,680 | A | * | 5/1999 | De Haan et al. ............... 382/265 |
| 5,911,012 | A | * | 6/1999 | Bernard et al. ................ 382/260 |
| 6,819,740 | B2 | | 11/2004 | Takahashi et al. ............ 378/98.8 |
| 6,847,408 | B1 | * | 1/2005 | Webb ............................. 348/607 |
| 7,929,031 | B2 | * | 4/2011 | Nakayama ..................... 348/241 |
| 8,319,897 | B2 | | 11/2012 | Kimura et al. ................. 348/607 |
| 2002/0101543 | A1 | * | 8/2002 | Ojo et al. ....................... 348/607 |
| 2002/0159649 | A1 | * | 10/2002 | Mollov et al. ................. 382/261 |
| 2004/0017880 | A1 | * | 1/2004 | Toth et al. .......................... 378/4 |
| 2004/0258325 | A1 | * | 12/2004 | Sasada .......................... 382/275 |
| 2005/0053306 | A1 | * | 3/2005 | Kuwabara ..................... 382/260 |
| 2006/0274877 | A1 | * | 12/2006 | Noshi et al. ....................... 378/4 |
| 2007/0071354 | A1 | * | 3/2007 | Florent et al. ................. 382/266 |
| 2008/0118128 | A1 | * | 5/2008 | Toth ............................... 382/131 |

(Continued)

FOREIGN PATENT DOCUMENTS

| CN | 100558144 C | 11/2009 |
| JP | 60-065679 | 4/1985 |

(Continued)

OTHER PUBLICATIONS

Office Action issued Apr. 26, 2013 in counterpart Korean Patent Application No. 10-2010-0133247, with partial translation.

(Continued)

*Primary Examiner* — Stephen R Koziol
*Assistant Examiner* — Jonathan S Lee
(74) *Attorney, Agent, or Firm* — Fitzpatrick, Cella, Harper & Scinto

(57) ABSTRACT

An information processing apparatus comprises: a spatial filtering unit configured to perform spatial filtering in a frequency range based on a spatial frequency of an object for image data of a current frame; and a recursive filtering unit configured to perform recursive filtering by obtaining image data, which has been processed prior to the current frame, from a memory, multiplying the obtained image data by a coefficient $\alpha$ ($\alpha<1$), adding the image data multiplied by the coefficient $\alpha$ to the image data of the current frame after the spatial filtering, and storing the image data after the addition in the memory.

13 Claims, 6 Drawing Sheets

(56) References Cited

U.S. PATENT DOCUMENTS

| | | | |
|---|---|---|---|
| 2008/0253679 A1* | 10/2008 | Takahashi | 382/261 |
| 2008/0303952 A1* | 12/2008 | Nakayama | 348/607 |
| 2009/0202129 A1* | 8/2009 | Omi | 382/132 |
| 2011/0019933 A1 | 1/2011 | Noda | 382/260 |
| 2011/0103673 A1* | 5/2011 | Rosenstengel | 382/132 |
| 2012/0263367 A1* | 10/2012 | Hoornaert | 382/132 |
| 2012/0275680 A1* | 11/2012 | Omi | 382/132 |
| 2013/0051527 A1* | 2/2013 | Sakaguchi et al. | 378/62 |

FOREIGN PATENT DOCUMENTS

| | | |
|---|---|---|
| JP | 63-271668 | 11/1988 |
| JP | 01273487 A * | 11/1989 |
| JP | H05-018714 | 1/1993 |
| JP | 05316468 A * | 11/1993 |
| JP | 10-1998-0703741 | 12/1998 |
| JP | 2003-204955 | 7/2003 |
| KR | 3159465 | 4/2001 |
| WO | WO 2007114470 A1 * | 10/2007 |

OTHER PUBLICATIONS

Office Action issued Jun. 14, 2013 by Chinese (P.R.C.) patent office in counterpart Chinese patent application 201010621807.9, with translation.

Office Action issued Dec. 19, 2013, in counterpart Chinese (PRC) patent application 2010106218070.9, with translation.

* cited by examiner

INFORMATION PROCESSING APPARATUS, PROCESSING METHOD, AND COMPUTER-READABLE STORAGE MEDIUM

BACKGROUND OF THE INVENTION

1. Field of the Invention

The present invention relates to an information processing apparatus, a processing method thereof, and a computer-readable storage medium.

2. Description of the Related Art

In recent years, medical diagnoses and treatments based on moving image capture which uses radiation (for example, X-rays) are being actively conducted. Nowadays, it is especially noteworthy that an X-ray imaging apparatus which uses a flat panel detector (obtained by forming an amorphous silicon TFT and a semiconductor sensor on a glass substrate) is frequently employed. However, a flat panel detector which uses an amorphous silicon TFT cannot amplify a photoelectrically converted signal by pixel by pixel, and therefore reads out a stored charge via a long signal line. Hence, noise is likely to be generated in the image under the influence of external or internal factors. It has recently been found that this noise includes both components with spatial frequencies which overlap those of an object, and components with spatial frequencies which have little overlap with those of the object.

Also, in imaging which uses radiation, a human body must be imaged at a low radiation dose in order to minimize the patient's exposure to the radiation. Hence, a signal with a very small value is read out, and even a slight fluctuation generated in the image is visually perceived. Vertically and horizontally running streaked variations (to be referred to as "line noise" hereinafter), for example, are sensitively perceived by the human eye and therefore exert a large influence on a diagnostic image.

A conventional technique to reduce line noise is a spatial filter, as disclosed in Japanese Patent Laid-Open No. 2003-204955 (to be referred to as "reference 1" hereinafter). In the technique described in reference 1, high-pass filtering is performed for an original image containing line noise in a direction perpendicular to the line noise. After that, low-pass filtering is horizontally performed for the processed image. As a result, a line noise image is obtained and is subtracted from the original image. Thus, the line noise remaining in the image is reduced.

Also, Japanese Patent Laid-Open No. 63-271668 (to be referred to as "reference 2" hereinafter) describes a technique of achieving noise reduction that generates only little blur and residue image by changing the mixture ratio between a spatial filter and a recursive filter in accordance with the degree of motion of the object. Moreover, Japanese Patent Laid-Open No. 60-065679 (to be referred to as "reference 3" hereinafter) describes a method of reducing line noise by calculating the difference between the current signal and a signal delayed by one scanning period, performing threshold processing and suppression processing, and adding the resulting processed signal to the current signal.

In the technique described in reference 1, the line noise undergoes spatial filtering and is thereby reduced. Unfortunately, this technique has only a small effect on line noise with low frequencies in a spatial frequency range nearly equal to that of the frequencies of the object.

Also, in the technique described in reference 2, an image that has undergone two-dimensional spatial filtering undergoes recursive filtering. However, the effect of recursive filtering is suppressed when the object is in motion, while the effect of two-dimensional spatial filtering is relatively great when the object is still. This technique cannot cope with, for example, noise which has spatial frequencies which overlap those of the object and which varies with time. Furthermore, in the technique described in reference 3, a signal delayed by one scanning period in a frame undergoes recursive filtering. Hence, this technique has a great effect on line noise with temporally high frequencies, but only a small effect on line noise with temporally low frequencies.

SUMMARY OF THE INVENTION

The present invention provides a technique which can reduce noise while suppressing the influence that radiation exerts on an object.

According to a first aspect of the present invention, there is provided an information processing apparatus comprising a spatial filtering unit configured to perform spatial filtering in a frequency range based on a spatial frequency of an object for image data of a current frame, and a recursive filtering unit configured to perform recursive filtering by obtaining image data that has been processed prior to the current frame, from a memory, multiplying the obtained image data by a coefficient $\alpha$ ($\alpha<1$), adding the image data multiplied by the coefficient $\alpha$ to the image data of the current frame after the spatial filtering, and storing the resulting processed image data (after the addition) in the memory.

According to a second aspect of the present invention, there is provided a processing method for an information processing apparatus, comprising performing spatial filtering in a frequency range based on a spatial frequency of an object for image data of a current frame, and performing recursive filtering by obtaining image data that has been processed prior to the current frame, from a memory, multiplying the obtained image data by a coefficient $\alpha$ ($\alpha<1$), adding the image data multiplied by the coefficient $\alpha$ to the image data of the current frame after the spatial filtering, and storing the resulting processed image data (after the addition) in the memory.

According to a third aspect of the present invention, there is provided a computer-readable storage medium storing a computer program which when executed will cause a computer to operate the above-described method.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention, and together with the description, serve to explain the principles of the invention.

DESCRIPTION OF THE EMBODIMENTS

Embodiments of the present invention will now be described in detail with reference to the drawings.

First Embodiment

Figure 1:
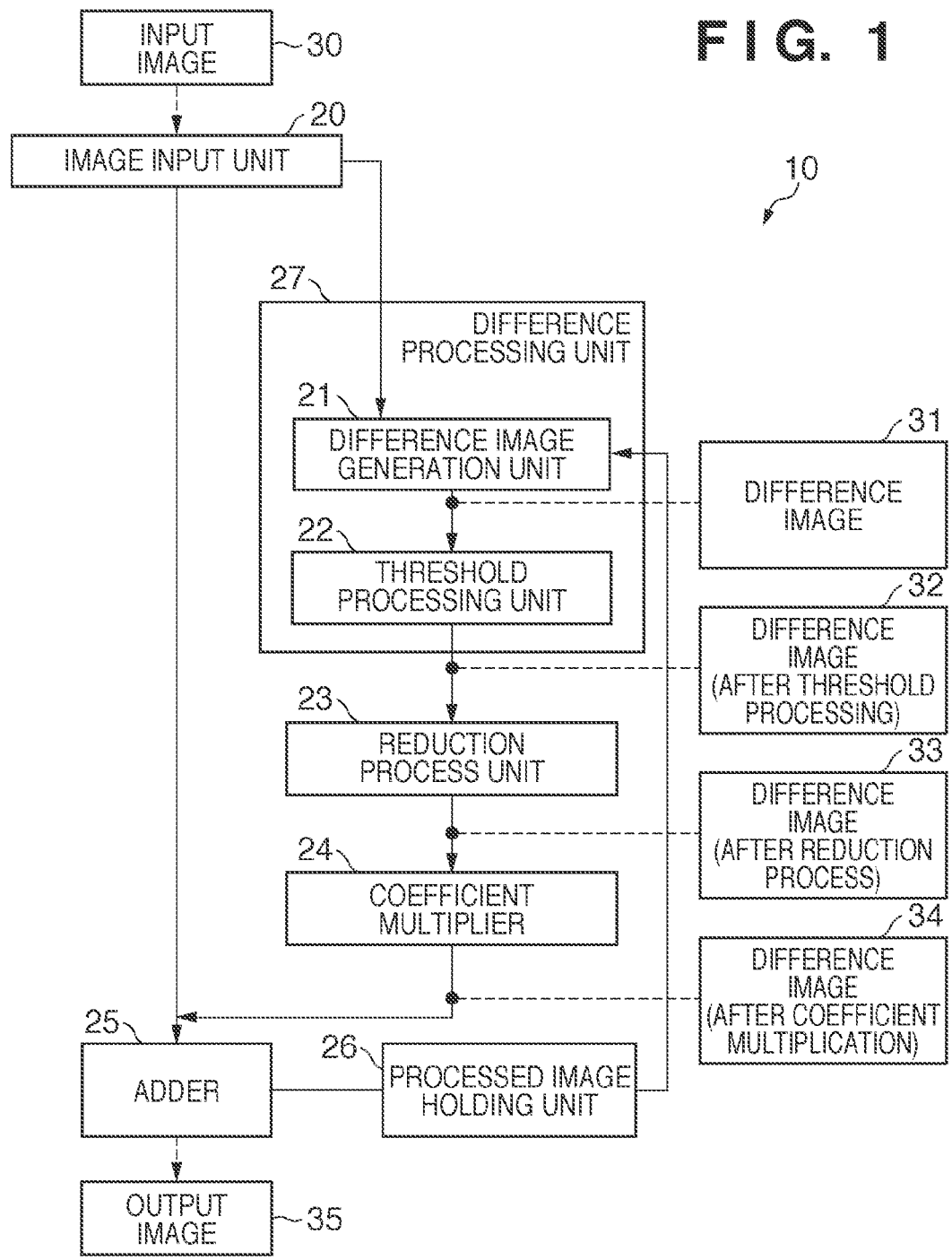
FIG. 1 is a block diagram showing an example of the configuration of an information processing apparatus according to a first embodiment of the present invention.

FIG. 1 is a block diagram showing an example of the functional configuration of an information processing apparatus according to a first embodiment of the present invention.

An information processing apparatus 10 includes one or a plurality of built-in computers. The computer includes, for example, a main control means such as a CPU, and storage means such as a ROM (Read Only Memory) and a RAM (Random Access Memory). The computer may also include a graphic control means such as a GPU (Graphics Processing Unit), a communication means such as a network card, and an input/output means such as a keyboard, a display or a touch panel. Note that these constituent means are connected via a bus, and controlled by executing programs stored in the storage means by the control means.

The information processing apparatus 10 includes an image input unit 20, reduction process unit 23, coefficient multiplier 24, adder 25, processed image holding unit 26, and difference processing unit 27 as its functional configuration. In this embodiment, random noise will be exemplified as noise with spatial frequencies which have little overlap with those of an object, and line noise (vertically and horizontally running streaked variations) will be exemplified as noise which has spatial frequencies which overlap those of the object but vary on the time axis.

The image input unit 20 externally inputs one frame (to be referred to as an "input image" hereinafter) of a moving image (continuous frames). That is, the image input unit 20 inputs image data of the current frame. An input image 30 is, for example, an n(rows)×m(columns) two-dimensional image. The input image 30 according to this embodiment contains line noise (vertically and horizontally running streaked variations) in a predetermined direction and an object, as indicated by hatched portions shown in FIG. 2B. Although a case in which the predetermined direction is the horizontal direction, and the noise discussed is horizontal line noise, will be exemplified in this embodiment, the predetermined direction may be the vertical direction, as a matter of course. Although the two-dimensional image is, for example, an image captured using X-rays, it need not always be an image captured using X-rays.

The processed image holding unit 26 functions as a memory which holds (stores) a previously processed, output image (an image one frame before the current frame in this embodiment). The difference processing unit 27 serves to generate a difference image, and includes a difference image generation unit 21 and threshold processing unit 22. The difference image generation unit 21 generates a difference image 31 between the input image 30 and the image held in the processed image holding unit 26 (that is, an output image 35 one frame before the current frame). Note that in processing the first frame in a moving image, an image identical to the input image 30 is output from the difference image 31 because there is no image one frame before this frame.

Figure 2A:
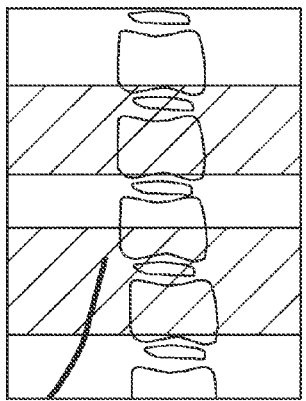
FIGS. 2A to 2F are views showing an overview of a line noise reduction process.
Figure 2B:
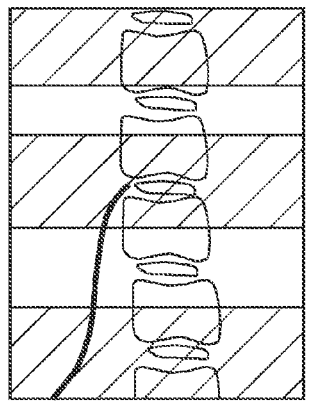
Figure 2C:
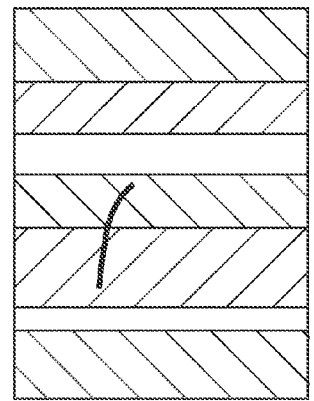

Note that the output image 35 one frame before the current frame contains line noise in the predetermined direction as well, as shown in FIG. 2A, and this noise normally varies with time. Therefore, line noise signals are generated in different regions in the images shown in FIGS. 2A and 2B. Although a case in which the images shown in FIGS. 2A and 2B have line noise signals with the same amplitude will be exemplified herein for the sake of descriptive simplicity, line noise signals that are actually generated in these images need not have temporally or spatially the same amplitude. The difference image 31 generated by the difference image generation unit 21 contains line noise (hatched portions), line noise (inversely hatched portions) with an amplitude inverse to that of the former noise, and a region in which an object has moved, as shown in FIG. 2C.

Figure 2D:
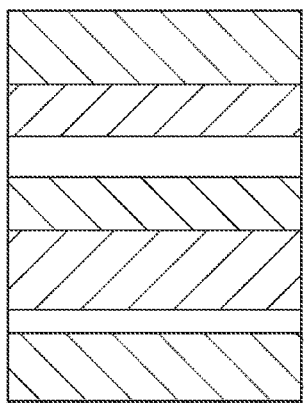

The threshold processing unit 22 performs threshold processing for the difference image 31 generated by the difference image generation unit 21. More specifically, the threshold processing unit 22 calculates the absolute value of each pixel in the difference image 31, and performs threshold processing for the absolute value using a predetermined value. For example, the predetermined value is set a value a little bigger than the standard deviation of the line noise. If the processing result shows that a pixel with an absolute value which exceeds the predetermined value is present, it is determined that this pixel represents a motion of the object, and this pixel is replaced with "0" or is multiplied by a coefficient smaller than "1". A difference image (after threshold processing) 32 obtained by this processing assumes a state in which the motion of the object is removed, as shown in FIG. 2D.

The difference image 31 contains random noise for each pixel in large amounts, so it is sometimes difficult to discriminate between a motion and random noise in this image. In this case, the threshold processing unit 22 may process the difference image 31 using, for example, a two-dimensional smoothing filter (spatial filtering) before the above-mentioned threshold processing. That is, the above-mentioned threshold processing is performed after random noise is reduced. With this processing, the rate of erroneous discrimination between random noise and a motion can be reduced, thus allowing motion determination with higher accuracy. Such spatial filtering is effective when the difference in spatial frequency between the noise and the object is small. The filtering range of this spatial filter is determined based on the spatial frequency of the object obtained from a frequency analysis unit (not shown). Thus, the noise can be reduced while information on the object is maintained in the image. The frequency analysis unit analyzes the frequency of the object using a known method such as Fourier transformation. Also, a value that is experimentally determined in advance may be used as the spatial frequency of the object.

Figure 2E:

The reduction process unit 23 functions as a noise image generation unit which generates a line noise image. That is, the reduction process unit 23 reduces the difference image (after threshold processing) 32 in the predetermined direction (the same direction as that in which the line noise runs), thereby generating a difference image (after a reduction process) 33 which contains line noise components as its principal components. The difference image (after a reduction process) 33 is reduced in the predetermined direction (horizontal direction). In this reduction process, respective pixels in the image (difference image (after threshold processing) 32) are, for example, linearly concatenated to each other in the predetermined direction (the horizontal direction in this embodiment). In the linear concatenation, the difference image (after threshold processing) 32 is horizontally reduced assuming the average of k pixels (k≥2) as one pixel. The reduction process may be, for example, a general decimation process. With this reduction process, random noise is averaged and is thereby reduced, so the difference image (after a reduction process) 33 which contains line noise components as its principal components is generated, as shown in FIG. 2E. The coefficient multiplier 24 multiplies each pixel in the difference image (after a reduction process) 33 by a coefficient α to generate a difference image (after coefficient multiplication) 34. The coefficient α is, for example, a value smaller than "1" (α<1). The frequency characteristics of a recursive filter in the time direction are determined in accordance with the value of this coefficient. Since the frequency characteristics of that filter in the time direction are determined in accordance with the magnitude of the coefficient α, the value of the coefficient α is experimentally determined such that the line noise can be separated from a motion of the object (for example, a human body). Alternatively, it is possible to extract the object and determine the value of the coefficient α from a motion of its edge portion in the time direction. Note that because the line noise temporally shifts with respect to a motion of the object (for example, a human body), it must be suppressed upon determining a filter in the time direction.

The adder 25 adds the difference image (after coefficient multiplication) 34 to the input image 30. The addition process may be performed after a reduced image is interpolated up to the size of the input image 30 using a commonly known interpolation method.

A pixel value Xt(i) of the input image 30, a pixel value Yt(i) of the output image 35 based on the input image 30, a pixel value Yt−1(i) of an output image one frame before the current frame, and a coefficient α by which each pixel is multiplied by the coefficient multiplier 24, have a relation:

$$Yt(i)=Xt(i)+\alpha F(Yt-1(i)-Xt(i)) \quad (1)$$

where F is a function representing, for example, threshold processing and a horizontal reduction process.

Figure 2F:
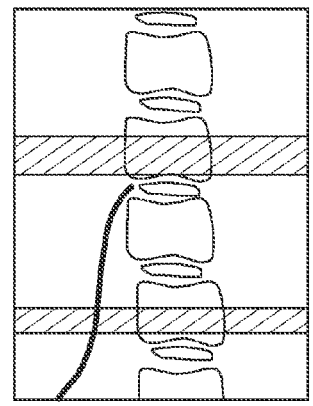

As a result, the line noise in the input image 30 is smoothed in the time direction in accordance with the coefficient α, as shown in FIG. 2F. Hatched portions in FIG. 2F indicate the state in which the line noise partially remains, but nonetheless the remaining noise indicated by the hatched portions is smoothed as frames are processed more.

In this manner, in this embodiment, recursive filtering is selectively performed for the line noise components, thus suppressing the line noise components in a series/sequence of moving images obtained as a result (that is, a plurality of output images 35).

An example of the sequence of a line noise reduction process in the information processing apparatus 10 shown in FIG. 1 will be described next with reference to FIG. 3.

When the information processing apparatus 10 uses the image input unit 20 to externally input one frame (input image 30) of a moving image (S101), this process starts. The input of a moving image may be done via, for example, a network or a storage medium such as a memory card.

Next, the information processing apparatus 10 uses the difference image generation unit 21 to generate a difference image (difference image 31) between the input image 30 and an image immediately before (that is, one frame before) the input image 30 (S102). Note that an image one frame before the input image 30 is obtained from the processed image holding unit 26.

After the generation of the difference image 31 is completed, the information processing apparatus 10 uses the threshold processing unit 22 to perform threshold processing for the generated difference image 31 (S103). After that, the information processing apparatus 10 uses the reduction process unit 23 to reduce a difference image (after threshold processing) 32 in a predetermined direction (horizontal direction in this example) (S104).

After the reduction process is completed, the information processing apparatus 10 uses the coefficient multiplier 24 to multiply each pixel in the difference image (after a reduction process) 33 by a coefficient (for example, a value smaller than "1") (S105). The frequency characteristics of a recursive filter in the time direction are determined in accordance with the value of this coefficient, as described earlier.

Lastly, the information processing apparatus 10 uses the adder 25 to add a difference image after the coefficient multiplication (after coefficient multiplication) 34 to the input image 30 input in step S101 (S106). Thus, after the addition, an output image 35 (that is, an image with less line noise) is obtained upon subtracting line noise from the input image 30.

An example of a line noise reduction effect in this embodiment will be described next with reference to FIG. 4.

Figure 4:
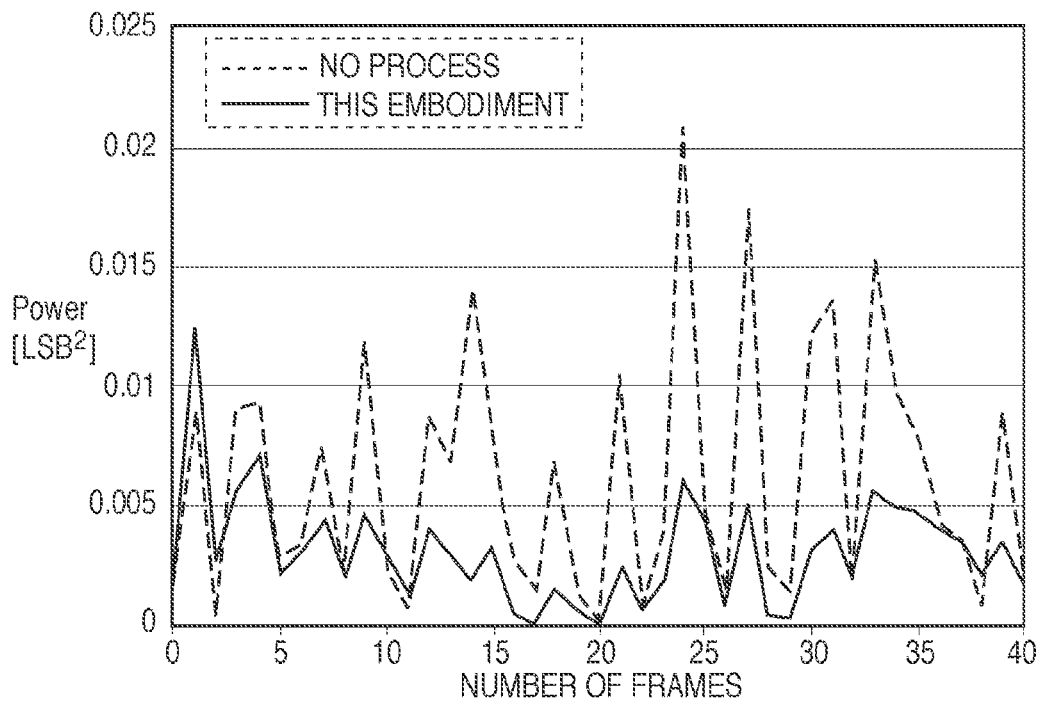
FIG. 4 is a graph showing a line noise reduction effect according to the first embodiment.

Referring to FIG. 4, the abscissa indicates the number of frames in a moving image, and the ordinate indicates the power spectrum of line noise. The power spectrum is calculated using a moving image with a pixel pitch of 300 μm and 1,000×1,000 pixels. Hence, the Nyquist frequency is 1.56 lp/mm The line noise having undergone power spectrum analysis is reduced into a range of frequencies as low as 7 lp/m, so the reduction process in this embodiment produces an effect up to a frequency range in which it is hard for a line noise reduction process which uses a conventional spatial filter to reduce the line noise. As can be seen from a comparison between the power spectrums in "no process (broken line)" and "this embodiment (solid line)", the power of the line noise is reduced to a half or less in this embodiment.

Second Embodiment

Figure 5:
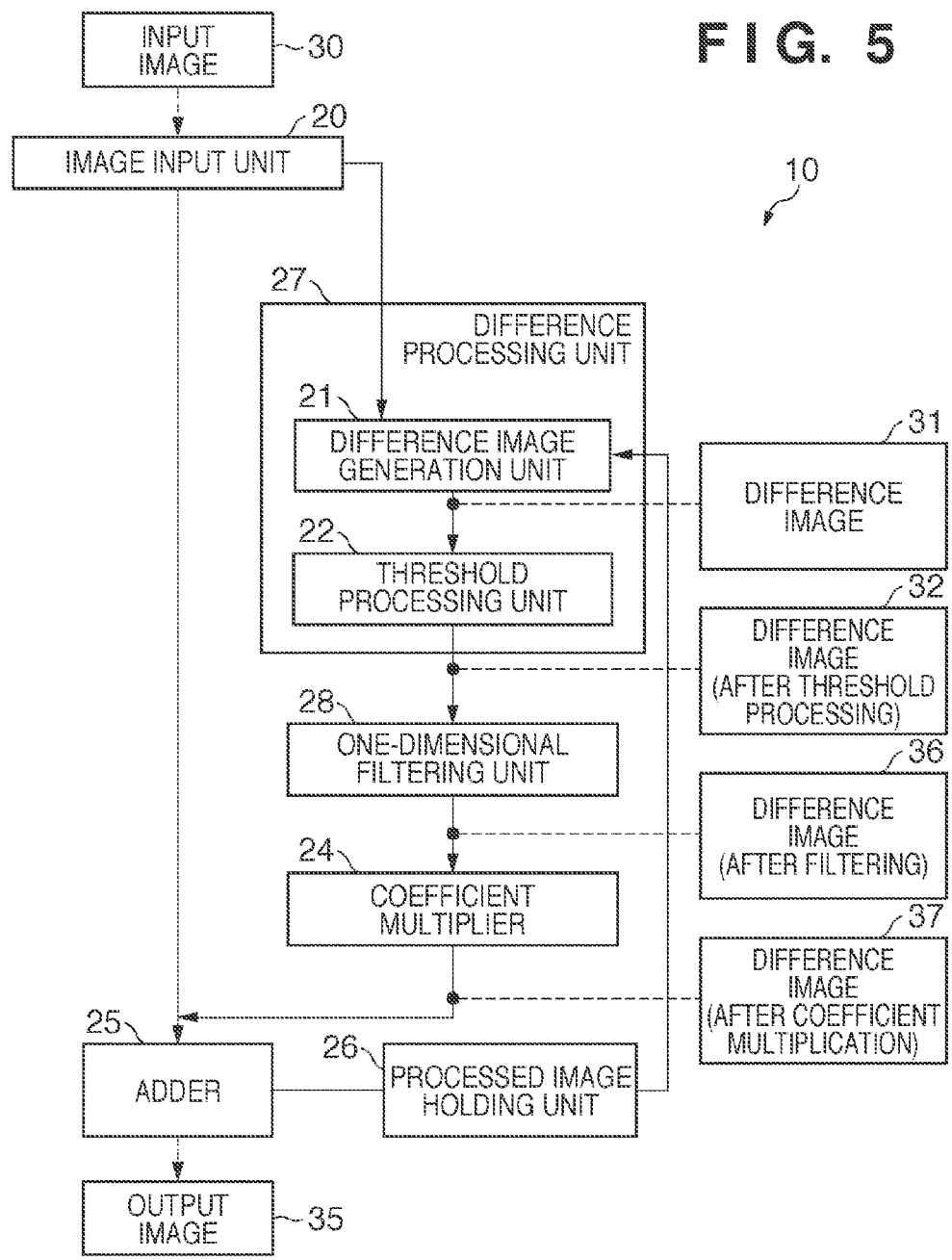
FIG. 5 is a block diagram showing an example of the configuration of an information processing apparatus according to a second embodiment.

The second embodiment will be described next. FIG. 5 is a block diagram showing an example of the functional configuration of an information processing apparatus 10 according to the second embodiment. Note that the same reference numerals denote constituent elements which exhibit the same functions as those in the functional configuration shown in FIG. 1 referred to in the description of the first embodiment, and a description thereof will sometimes not be given. The difference between the first and second embodiments will be mainly described herein.

The information processing apparatus 10 includes an image input unit 20, coefficient multiplier 24, adder 25, processed image holding unit 26, difference processing unit 27, and one-dimensional filtering unit 28. That is, the information processing apparatus 10 is obtained by omitting the reduction process unit 23 from the configuration shown in FIG. 1 referred to in the description of the first embodiment, and adding the one-dimensional filtering unit 28 to this configuration.

The one-dimensional filtering unit 28 functions as a noise image generation unit which generates a line noise image. That is, the one-dimensional filtering unit 28 performs one-dimensional smoothing filtering for a difference image 32 in a predetermined direction (the same direction as that in which the line noise runs), thereby generating a difference image (after filtering) 36 which contains line noise components as its principal components. A one-dimensional smoothing filter may be a commonly known filter such as an averaging filter, a Gaussian filter, or a median filter. With this filtering, random noise is averaged and is thereby reduced, so the difference image (after filtering) 36 which contains line noise components as its principal components is generated.

After the filtering, the information processing apparatus 10 uses the coefficient multiplier 24 to multiply the difference image (after filtering) 36 by a coefficient, and uses the adder 25 to add a difference image (after coefficient multiplication) 37 to an input image 30. Thus, in the second embodiment, as well as the first embodiment, recursive filtering can be selectively performed for the line noise.

Figure 3:
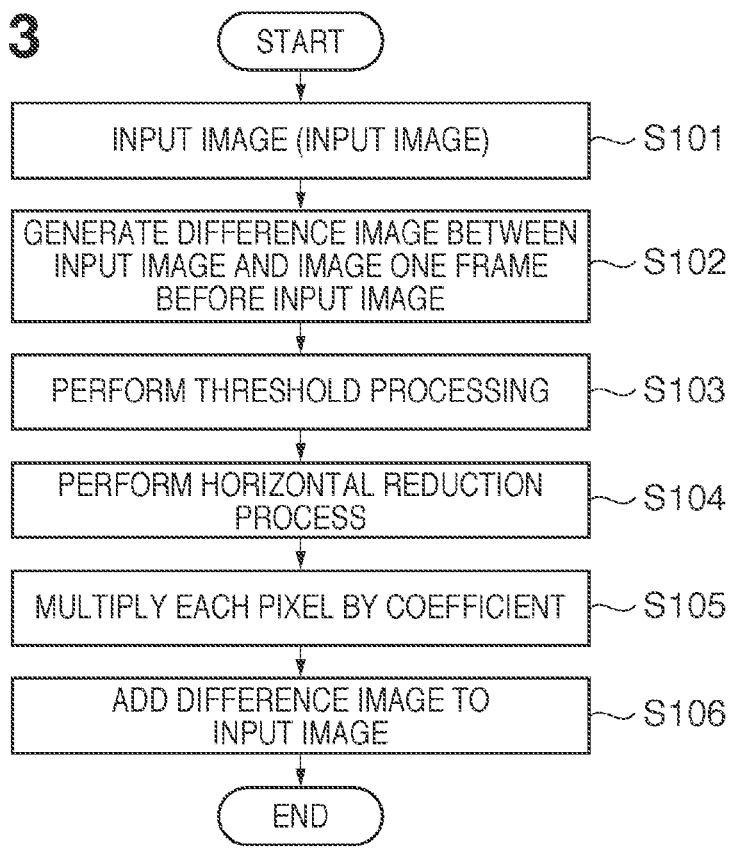
FIG. 3 is a flowchart showing an example of the sequence of the information processing apparatus 10 shown in FIG. 1.

Note that the operation of the information processing apparatus 10 according to the second embodiment follows the same process sequence as in FIG. 3 referred to in the description of the first embodiment, and a description thereof with reference to drawings will not be given. A difference between the first and second embodiments lies in that in the latter the above-mentioned one-dimensional filtering is performed in step S104, instead of the horizontal reduction process in the former.

Third Embodiment

The third embodiment will be described next, in which the noise reduction processes described in the first and second embodiments uses a spatial filter as described in reference 1 are performed in combination will be exemplified in the third embodiment.

Figure 6:
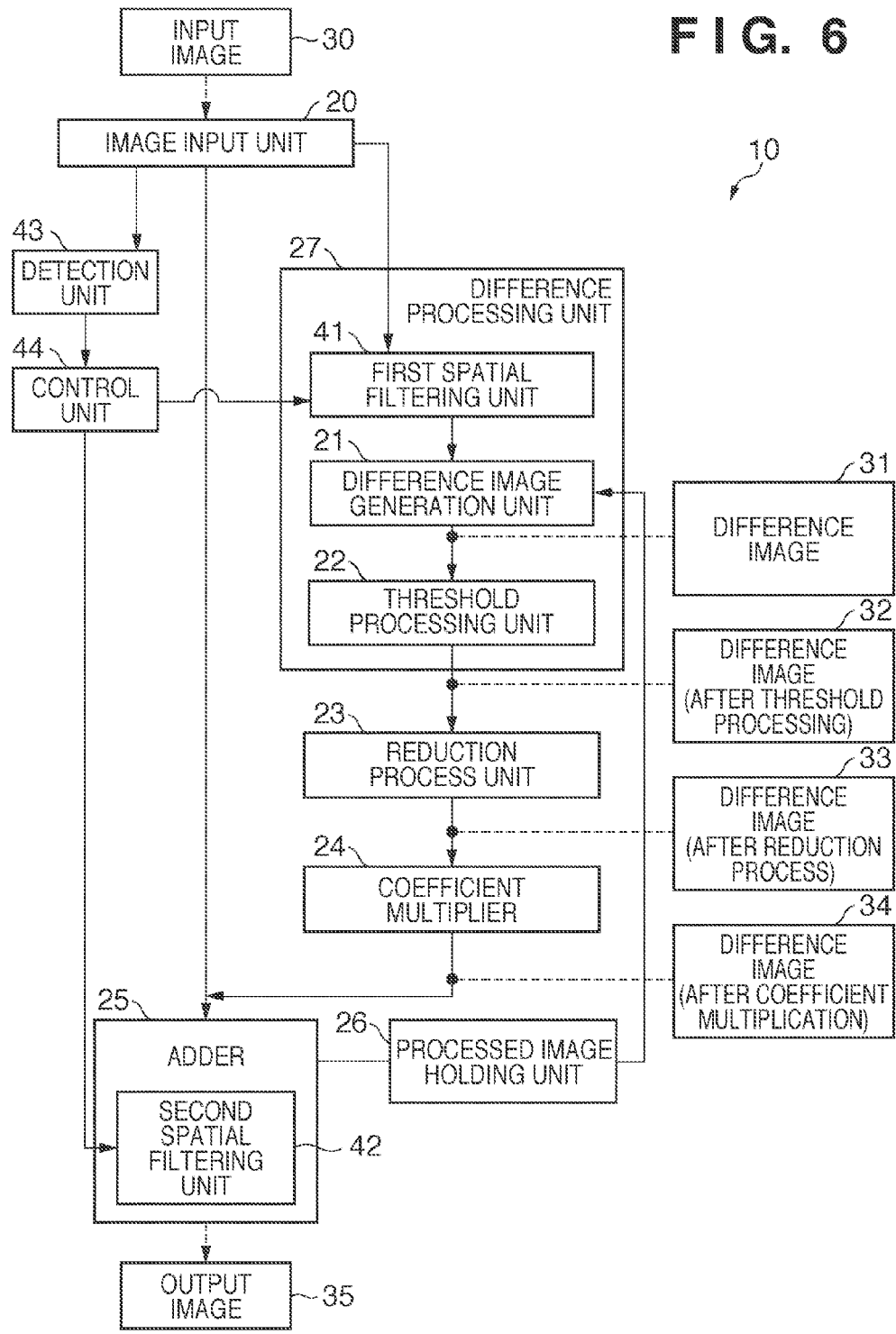
FIG. 6 is a block diagram showing an example of the configuration of an information processing apparatus according to a third embodiment.

FIG. 6 is a block diagram showing an example of the functional configuration of an information processing apparatus 10 according to the third embodiment. Note that the same reference numerals denote constituent elements which exhibit the same functions as those in the functional configuration shown in FIG. 1 referred to in the description of the first embodiment, and a description thereof will sometimes not be given. A difference between the first and third embodiments will be mainly described herein.

The information processing apparatus 10 includes a first spatial filtering unit 41, second spatial filtering unit 42, detection unit 43, and control unit 44, in addition to the configuration shown in FIG. 1 referred to in the description of the first embodiment.

The first spatial filtering unit 41 performs a noise reduction process which uses a spatial filter for an input image 30. When, for example, the motion of the object is large and the influence of a image lag is non-negligible, the noise reduction processes described in the first and second embodiment are performed after a noise reduction process which uses a spatial filter is performed by the first spatial filtering unit 41. In this case, because a predetermined value (threshold) used for a threshold processing unit 22 can be made small, an image with little residue image can be obtained. That is, the noise reduction process by the first spatial filtering unit 41 is effective when the motion of the object is large and the influence of a residue image is non-negligible. Note that the noise reduction process which uses a spatial filter may employ a conventional technique (for example, reference 1), and a description thereof will not be given.

The second spatial filtering unit 42 performs a noise reduction process which uses a spatial filter for an image processed by an adder 25. That is, the second spatial filtering unit 42 performs the same process as in the first spatial filtering unit 41 although they process different images. For example, after the noise reduction processes described in the first and second embodiments are performed, the second spatial filtering unit 42 analyzes the spatial frequency components of the remaining line noise. After that, the second spatial filtering unit 42 performs a noise reduction process which uses a spatial filter for the spatial frequencies obtained by this analysis. In this case, there is no need to perform spatial filtering over an unnecessarily wide range. For example, as for the nature description image, the spatial frequency component of the low frequency is important. Thus, it possible to prevent the object from blurring, if the noise reduction process by the second spatial filtering unit 42 is set a limit in high spatial frequency component.

The detection unit 43 detects the intensity of line noise and a motion of the object, both in the input image 30. Note that the detection of the intensity of line noise and a motion of the object may employ a conventional technique (for example, reference 2), a description thereof will not be given.

According to the configuration described above, a noise reduction process which uses a spatial filter is performed before or after execution of the noise reduction processes described in the first and second embodiments, in accordance with the intensity of line noise and a motion of the object. Thus, line noise reduction processes are adaptively performed, so a moving image with little residue image and object blur can be obtained. That is, the noise can be reduced while suppressing the influence that radiation exerts on the object.

The configuration of the information processing apparatus 10 according to the third embodiment shown in FIG. 6 is merely an example, and can be appropriately changed. The detection unit 43 and control unit 44, for example, are not indispensable constituent elements and may be omitted. When these constituent elements are omitted, processes by the first spatial filtering unit 41 and second spatial filtering unit 42 are uniformly performed. Also, not both the first spatial filtering unit 41 and second spatial filtering unit 42, for example, need be provided, and only one of them may be provided.

Figure 7:
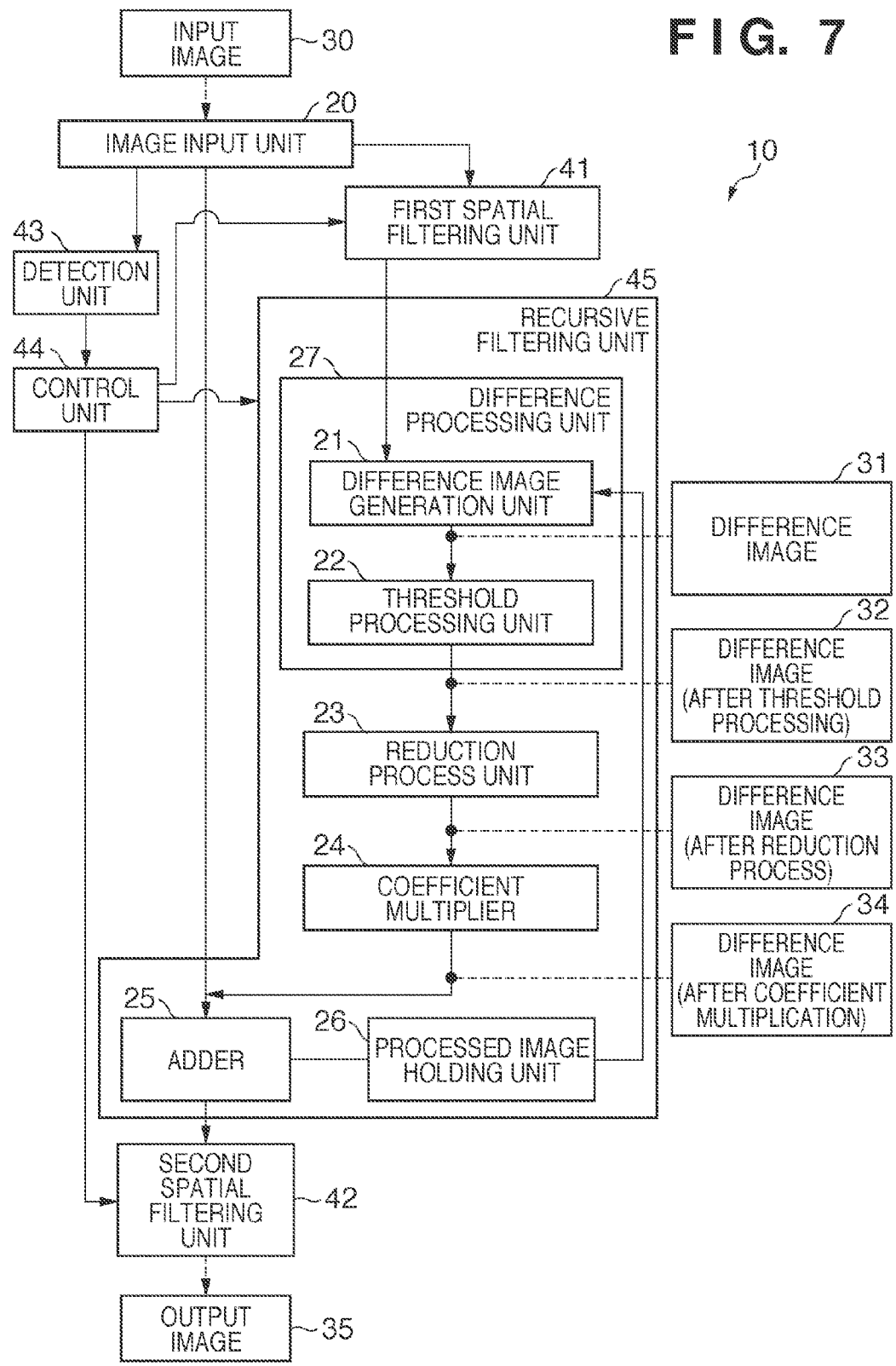
FIG. 7 is a block diagram showing another example of the configuration of an information processing apparatus according to the third embodiment.

Moreover, as in reference 2, a configuration which performs first noise reduction processes as described in the first and second embodiments and a second noise reduction process which uses a spatial filter while changing the process ratio, for example, may be adopted. This configuration can be realized by adopting a configuration shown in, for example, FIG. 7. That is, a control unit 44 executes a first noise reduction process by a recursive filtering unit 45, and a second noise reduction process which uses a spatial filter while changing the process ratio, in accordance with the detection results obtained by a detection unit 43. Note that the change in process ratio takes place based on the intensity of line noise and on a motion of the object. In this case, noise reduction processes are adaptively performed, so a moving image with little residue image and object blur can be obtained.

Although exemplary embodiments of the present invention have been described above, the present invention is not limited to the embodiments described above and shown in the drawings, and can be appropriately modified and practiced without departing from the scope of the present invention.

As an example, although a case in which an image one frame before the current frame is used in difference processing has been exemplified in the first and second embodiments, the present invention is not limited to this, and an image more than one frame before the current frame or a plurality of images of two or more different frames, for example, may be used. For example, it depends and can perform the disposal for free time frequency component if it seems to be general recursive filter and handles it with plural frames.

As another example, although only image data of a frame processed prior to the current frame is multiplied by the coefficient $\alpha$ (a multiple of the coefficient $\alpha$) in the first to third embodiments, the present invention is not limited to this. For example, image data of the current frame may be multiplied by a value corresponding to the coefficient α by which image data of a frame processed prior to the current frame is multiplied.

The present invention can be embodied as, for example, a system, an apparatus, a method, and a program or a storage medium. More specifically, the present invention may be applied to a system including a plurality of devices or an apparatus including only one device.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-293208 filed on Dec. 24, 2009, which is hereby incorporated by reference herein in its entirety.

What is claimed is:

1. An information processing apparatus for noise reduction for an X-ray moving image including a plurality of X-ray frame images, the apparatus comprising:
    a difference processing unit including a processor configured to generate a difference image between a current X-ray frame image and a processed X-ray image obtained from previous X-ray frame images and stored in a memory;
    an extraction unit including a processor configured to extract a noise image based on the difference image;
    a calculation processing unit including a processor configured to mix the current X-ray frame image and the noise image with a specific mixture ratio, to obtain a noise-reduced image; and
    a storage unit configured to store the noise-reduced image in the memory as a new processed image to be provided to the difference processing unit.

2. The apparatus according to claim 1, wherein said extraction unit extracts line noise running in a predetermined direction in said difference image.

3. The apparatus according to claim 2, wherein said extraction unit extracts the line noise by smoothing the difference image in the predetermined direction.

4. The apparatus according to claim 1, further comprising:
    a spatial filtering unit including a processor configured to perform spatial filtering processing for a current X-ray frame image based on object information before generating the difference image; and
    a motion reduction processing unit including a processor configured to remove motion information of the object in the difference image generated by said difference processing unit after the spatial filtering processing,
    wherein said extraction unit extracts the noise image from the image from which the motion information is reduced.

5. The apparatus according to claim 4, further comprising a second spatial filtering unit configured to perform spatial filtering processing based on image information of the image obtained by said calculation processing unit, for the image obtained by said calculation processing unit.

6. The apparatus according to claim 4, further comprising a determination unit including a processor configured to determine a processing ratio between the processing by said spatial filtering unit and the processing by said calculation processing unit based on at least one of the motion information and object information of the current X-ray frame image,
    wherein at least one of a parameter of the spatial filtering processing by said spatial filtering unit and the specific mixture ratio by said calculation processing unit is changed based on the determined processing ratio.

7. The apparatus according to claim 1, further comprising a determination unit including a processor configured to determine the specific mixture ratio based on an amount of the motion of the object in the moving X-ray image.

8. The apparatus according to claim 1, wherein said difference processing unit generates a difference image between another X-ray frame image and the new processed X-ray image stored in the memory.

9. An information processing apparatus for noise reduction for an X-ray moving image including a plurality of X-ray frame images, the apparatus comprising:
    a difference processing unit including a processor configured to generate a difference image between a current X-ray frame image and a processed X-ray image obtained from previous X-ray frame images and stored in a memory;
    an extraction unit including a processor configured to extract a noise image based on the difference image;
    a calculation processing unit including a processor configured to mix the current X-ray frame image and the noise image with a specific mixture ratio, to obtain a noise-reduced image for the current X-ray frame image; and
    a storage unit configured to store the noise-reduced image as a new processed X-ray image in the memory,
    wherein said difference processing unit is configured to receive a next X-ray frame image and the new processed X-ray image obtained by said calculation processing unit, for obtaining a noise-reduced image for a noise-reduced image for the next X-ray frame image.

10. A processing method for an information processing apparatus for noise reduction for an X-ray moving image including a plurality of X-ray frame images, the method comprising:
    generating a difference image between a current X-ray frame image and a processed X-ray image obtained from previous X-ray frame images and stored in a memory;
    extracting a noise image based on the difference image;
    mixing the current X-ray frame image and the noise image with a specific mixture ratio, to obtain a noise-reduced image; and
    storing the noise-reduced image in the memory as a new processed image to be provided to a difference processing unit for performance thereon of said generating step.

11. A processing method for an information processing apparatus for noise reduction for an X-ray moving image including a plurality of X-ray frame images, the method comprising:

generating a difference image between a current X-ray frame image and a processed X-ray image obtained from previous X-ray frame images and stored in a memory;

extracting a noise image based on the difference image;

mixing the current X-ray frame image and the noise image with a specific mixture ratio, to obtain a noise-reduced image for the current X-ray frame image; and storing the noise-reduced image as a new processed X-ray image in the memory, wherein a next X-ray frame image and the new processed X-ray image obtained by the mixing are received in a generating unit for performance thereon of said generating step, for obtaining a noise-reduced image for a noise-reduced image for the next X-ray frame image.

12. A non-transitory computer-readable storage medium storing a computer program which when executed will cause a computer to perform the method of claim 10.

13. A non-transitory computer-readable storage medium storing a computer program which when executed will cause a computer to perform the method of claim 11.

* * * * *